United States Patent
Takahashi et al.

(10) Patent No.: US 9,144,523 B2
(45) Date of Patent: Sep. 29, 2015

(54) ABSORBENT PRODUCT AND METHOD OF MANUFACTURING ABSORBENT PRODUCT

(75) Inventors: Yuki Takahashi, Mima-gun (JP); Emi Amano, Mima-gun (JP)

(73) Assignee: LIVEDO CORPORATION, Shikokuchuo-shi (JP)

( * ) Notice: Subject to any disclaimer, the term of this patent is extended or adjusted under 35 U.S.C. 154(b) by 147 days.

(21) Appl. No.: 13/883,624

(22) PCT Filed: Nov. 7, 2011

(86) PCT No.: PCT/JP2011/006210
§ 371 (c)(1),
(2), (4) Date: May 6, 2013

(87) PCT Pub. No.: WO2012/063460
PCT Pub. Date: May 18, 2012

(65) Prior Publication Data
US 2013/0226127 A1    Aug. 29, 2013

(30) Foreign Application Priority Data

Nov. 10, 2010    (JP) ................................ 2010-251724

(51) Int. Cl.
*A61F 13/49*    (2006.01)
*A61F 13/494*    (2006.01)
*A61F 13/15*    (2006.01)

(52) U.S. Cl.
CPC ..... *A61F 13/49406* (2013.01); *A61F 13/15593* (2013.01); *A61F 13/15699* (2013.01); *A61F 13/15739* (2013.01); *A61F 13/15804* (2013.01);

(Continued)

(58) Field of Classification Search
CPC ................... A61F 13/49011; A61F 13/49012; A61F 2013/49033
USPC ..................................................... 604/385.29
See application file for complete search history.

(56) References Cited

U.S. PATENT DOCUMENTS 5,746,731 A * 5/1998 Hisada ........................ 604/385.3
5,817,087 A * 10/1998 Takabayashi et al. ... 604/385.29

(Continued)

FOREIGN PATENT DOCUMENTS

| CN | 1391876 A | 1/2003 |
|---|---|---|
| CN | 101346120 A | 1/2009 |

(Continued)

OTHER PUBLICATIONS

International Search Report for PCT/JP2011/006210, mailing date of Mar. 6, 2012.

*Primary Examiner* — Susan Su
(74) *Attorney, Agent, or Firm* — Westerman, Hattori, Daniels & Adrian, LLP

(57) ABSTRACT

In a disposable diaper in a developed state where a front cover sheet and a rear cover sheet are separated from each other to be developed, as distance in a left-right direction from an absorbent body increases, a lower edge of the rear cover sheet goes away from an upper edge of the rear cover sheet and then goes toward the upper edge. A leg elastic member is bonded on the rear cover sheet along its lower edge, in left and right of the absorbent body. As above, the lower end portion of the rear cover sheet is convex downward in each of left and right of the absorbent body, and lower portions of hips of a wearer are wrapped with the lower end portions. It is therefore possible to suppress leakage of excrement from the lower portions of hips of the wearer.

12 Claims, 10 Drawing Sheets

(52) U.S. Cl.
CPC ..... *A61F 13/49058* (2013.01); *Y10T 156/1051* (2015.01)

(56) References Cited

U.S. PATENT DOCUMENTS

| | | | |
|---|---|---|---|
| 5,916,206 A * | 6/1999 | Otsubo et al. | 604/385.27 |
| 6,364,863 B1 * | 4/2002 | Yamamoto et al. | 604/385.27 |
| 7,060,058 B2 | 6/2006 | Otsubo et al. | |
| 2001/0016723 A1 * | 8/2001 | Sayama et al. | 604/398 |
| 2002/0147438 A1 * | 10/2002 | Tanaka et al. | 604/392 |
| 2002/0147439 A1 * | 10/2002 | Tanaka et al. | 604/398 |
| 2002/0151864 A1 | 10/2002 | Otsubo et al. | |
| 2004/0133181 A1 * | 7/2004 | Ishiguro et al. | 604/385.28 |
| 2005/0010188 A1 | 1/2005 | Glaug et al. | |
| 2006/0036227 A1 * | 2/2006 | Hoshino et al. | 604/385.3 |
| 2009/0071600 A1 | 3/2009 | Wada | |
| 2010/0262110 A1 * | 10/2010 | Lakso | 604/385.3 |
| 2011/0048618 A1 | 3/2011 | Makimura | |

FOREIGN PATENT DOCUMENTS

| | | |
|---|---|---|
| EP | 1 970 036 A1 | 9/2008 |
| JP | 10-243961 A | 9/1998 |
| JP | 11-047189 A | 2/1999 |
| JP | 11-188061 A | 7/1999 |
| JP | 3051733 B1 | 6/2000 |
| JP | 3916878 B2 | 5/2007 |
| JP | 2008-284058 A | 11/2008 |
| WO | 2007/145130 A1 | 12/2007 |
| WO | 2009/147957 A1 | 12/2009 |

* cited by examiner

IV—IV

ABSORBENT PRODUCT AND METHOD OF MANUFACTURING ABSORBENT PRODUCT

TECHNICAL FIELD

The present invention relates to an absorbent product and a method of manufacturing an absorbent product.

BACKGROUND ART

A pants-type disposable diaper which has a waist opening at an upper end and a pair of leg openings on a lower part is conventionally used as one type of absorbent product for receiving excrement from a wearer. For example, in Japanese Patent Publication No. 3051733 (Document 1), disclosed is a disposable underpants where edges of leg openings in a front part are formed by cutting deeply in comparison with edges of leg openings in a rear part.

In Japanese Patent Publication No. 3916878 (Document 2), a method of manufacturing a pants-type disposable diaper is disclosed. In the method of Document 2, a pair of leg elastic members is bonded, in a sine wave form, on strip-like web, and the web is cut between the pair of leg elastic members to form two half webs. Subsequently, the two half webs are brought away from each other, and a plurality of absorbent pads are located between these half webs to be bonded thereon. These absorbent pads are half-folded to lay the two half webs on each other. The two half webs are bonded to each other at bonding positions between the plurality of absorbent pads and the half webs are cut at the bonding positions to form disposable diapers.

On the other hand, in International Publication No. WO 2007/145130 (Document 3), disclosed is a belt-type disposable diaper where left and right side portions of a front part and left and right side portions of a rear part are connected with fastening tapes to be worn. The disposable diaper of Document 3 is manufactured by a manufacturing method similar to the method of Document 2. In the manufacturing method of Document 3, steps of Document 2 to lay the two half webs on each other and bond them between the plurality of absorbent pads are omitted.

In the disposable underpants of Document 1, in a cover sheet bonded on an outer surface of an absorbent body, as distance in a left-right direction from the absorbent body increases, a lower edge of the rear part to be positioned on the back side of a wearer (i.e., the lower edge including parts of edges of the leg openings) goes toward its upper edge (i.e., the upper edge included in the edge of the waist opening). Ditto with the disposable diapers of Document 2 and Document 3, out of two cover sheets to which end portions of the absorbent pad are bonded, a lower edge of one cover sheet to be positioned on the back side of a wearer goes toward its upper edge as distance in the left-right direction from the absorbent body increases.

Thus, in the disposable diapers of Document 1 to Document 3, it is difficult to fully wrap the hips of the wearer with the cover sheet. Therefore, lower portions of the hips (i.e., the neighborhoods of borders between the hips and thighs) are exposed at positions below the disposable diaper (i.e., the lower portions are not covered with the disposable diaper.) and there is a possibility that excrement leaks out to the positions.

SUMMARY OF INVENTION

The present invention is intended for an absorbent product. It is an object of the present invention to suppress leakage of excrement from lower portions of the hips of a wearer.

The absorbent product according to the present invention comprises: a rear cover sheet; a front cover sheet whose both side portions in a left-right direction are bonded or connectable to both side portions of the rear cover sheet in the left-right direction; an absorbent body which extends from a front middle portion of the front cover sheet to a rear middle portion of the rear cover sheet via a crotch portion of a wearer when worn, the front middle portion being a middle portion in the left-right direction, the rear middle portion being a middle portion in the left-right direction; waist elastic members which are bonded on the front cover sheet and the rear cover sheet along an upper edge of the front cover sheet and an upper edge of the rear cover sheet; and leg elastic members which are bonded on the front cover sheet and the rear cover sheet in left and right of the absorbent body, the leg elastic members lying along a lower edge of the front cover sheet and a lower edge of the rear cover sheet; wherein in a developed state where the front cover sheet and the rear cover sheet are separated from each other to be developed, as distance in the left-right direction from the absorbent body increases, the lower edge of the rear cover sheet goes away from the upper edge of the rear cover sheet and then goes toward the upper edge.

In the present invention, it is possible to suppress leakage of excrement from lower portions of the hips of a wearer.

According to a preferred embodiment of the present invention, in a developed state where the front cover sheet and the rear cover sheet are separated from each other to be developed, as distance in the left-right direction from the absorbent body increases, the lower edge of the front cover sheet goes toward the upper edge of the front cover sheet and then goes away from the upper edge. It is therefore possible to prevent the front cover sheet from interfering with leg movement of the wearer.

In this case, it is preferable that the lower edge of the front cover sheet has a shape to fit a shape of the lower edge of the rear cover sheet when the front cover sheet and the rear cover sheet are brought close to each other.

According to another preferred embodiment of the present invention, the absorbent product further comprises: body-fitting elastic members extending in the left-right direction, lying between the waist elastic members and the leg elastic members and being bonded on the front cover sheet and the rear cover sheet; and a rear auxiliary elastic member having a same shape with a leg elastic member bonded on the rear cover sheet, lying between a body-fitting elastic member and the leg elastic member and being bonded on the rear cover sheet at a certain distance away from the leg elastic member.

The present invention is also intended for a method of manufacturing an absorbent product. The method comprises the steps of: a) forming a sheet member by locating a pair of leg elastic members on a strip-like first sheet and bonding a strip-like second sheet on the first sheet with the pair of leg elastic members between the first sheet and the second sheet while conveying the first sheet in a predetermined conveying direction, the pair of leg elastic members windingly extending along the conveying direction and being located a certain distance away from each other in a width direction orthogonal to the conveying direction; b) forming a front-cover-sheet continuous body and a rear-cover-sheet continuous body by cutting the sheet member between the pair of leg elastic members; c) bringing the front-cover-sheet continuous body and the rear-cover-sheet continuous body away from each other in the width direction and sequentially locating a plurality of absorbent bodies between the front-cover-sheet continuous body and the rear-cover-sheet continuous body, to bond the plurality of absorbent bodies to the front-cover-sheet continuous body and the rear-cover-sheet continuous body; and d) sequentially forming absorbent products by sequentially folding the plurality of absorbent bodies to lay the front-cover-sheet continuous body on the rear-cover-sheet continuous body, bonding the front-cover-sheet continuous body and the rear-cover-sheet continuous body to each other at bonding positions between the plurality of absorbent bodies, and cutting the front-cover-sheet continuous body and the rear-cover-sheet continuous body at the bonding positions; wherein in a rear cover sheet, which is a portion of the rear-cover-sheet continuous body, of each absorbent product, as distance on each side of the conveying direction from an absorbent body increases, a cut edge formed by cutting in the step b) goes away from an outer edge of the rear-cover-sheet continuous body in the width direction and then goes toward the outer edge, and in a front cover sheet, which is a portion of the front-cover-sheet continuous body, of the each absorbent product, as distance on each side of the conveying direction from the absorbent body increases, a cut edge formed by cutting in the step b) goes toward an outer edge of the front-cover-sheet continuous body in the width direction and then goes away from the outer edge.

These and other objects, features, aspects and advantages of the present invention will become more apparent from the following detailed description of the present invention when taken in conjunction with the accompanying drawings.

DESCRIPTION OF EMBODIMENTS

Figure 1:
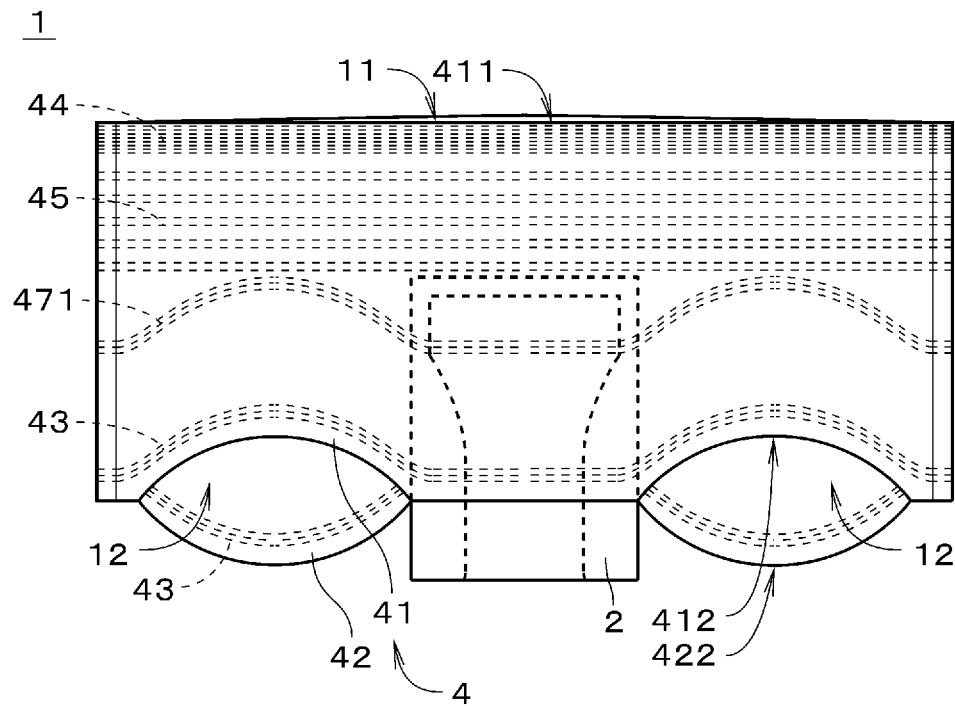
FIG. 1 is a front view of a disposable diaper in accordance with a preferred embodiment.
Figure 2:
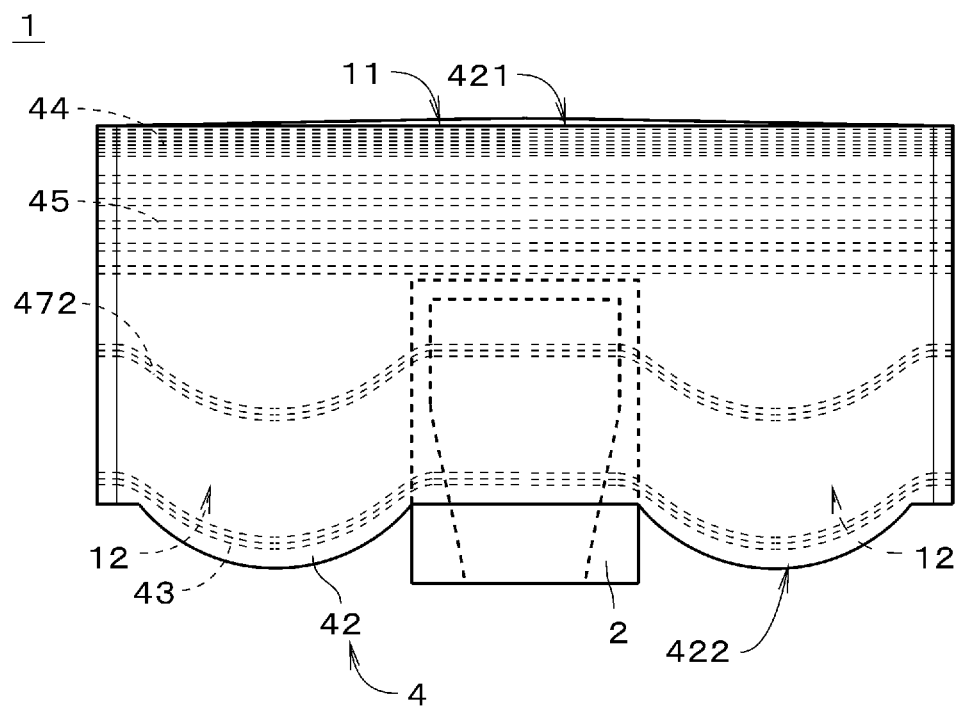
FIG. 2 is a rear view of the disposable diaper.

FIGS. 1 and 2 are a front view and rear view of a disposable diaper 1 in accordance with a preferred embodiment of the present invention, respectively (i.e., the front view and rear view are views of a portion to be positioned on the front side (stomach side) of a wearer and a portion to be positioned on the back side.). As shown in FIGS. 1 and 2, the disposable diaper 1 is a pants-type (i.e., pull-up type) absorbent product which has a waist opening 11 at an upper end (i.e., an end on the upper side in FIGS. 1 and 2) and a pair of leg openings 12 on a lower part, and it receives excrement from a wearer.

The disposable diaper 1 has a round cover sheet (outer covering sheet) 4 and an absorbent body 2 bonded on the wearer's side of the cover sheet 4 so as to cross over a lower opening of the cover sheet 4 (i.e., the lower opening is an opening different from an upper opening which is the waist opening 11.). The cover sheet 4 has a front cover sheet 41 to be positioned on skin of the front side of the wearer and a rear cover sheet 42 to be positioned on skin of the back (rear) side of the wearer. Both side portions of the front cover sheet 41 in a left-right direction are bonded to both side portions of the rear cover sheet 42 in the left-right direction by heat-sealing or the like. When the disposable diaper 1 is worn, the absorbent body 2 extends from a front middle portion of the front cover sheet 41 to a rear middle portion of the rear cover sheet 42 via the crotch portion of the wearer where the front middle portion is a middle portion in the left-right direction and the rear middle portion is a middle portion in the left-right direction. The absorbent body 2 protrudes downwards from a lower end of the cover sheet 4 and faces the crotch portion of the wearer to absorb excrement from the wearer.

The disposable diaper 1 further has leg elastic members 43, waist elastic members 44 and body-fitting elastic members 45 (i.e., elastic members to bring the disposable diaper 1 into close contact with the body of the wearer) which are bonded on the front cover sheet 41 and the rear cover sheet 42. Each of the front cover sheet 41 and the rear cover sheet 42 has a plurality of sheets (two sheets in the present embodiment) which are laminated, and the leg elastic member 43, the waist elastic member 44 and the body-fitting elastic member 45 are located between the two sheets to be bonded thereto with hot melt adhesive in a state where they are stretched.

The leg elastic members 43 in left and right of the absorbent body 2 windingly extend in the left-right direction along a lower edge 412 of the front cover sheet 41 and a lower edge 422 of the rear cover sheet 42 (i.e., each lower edge is parts of edges of the pair of leg openings 12.). The waist elastic members 44 extend almost straight in nearly parallel with the left-right direction and lie along an upper edge 411 of the front cover sheet 41 and an upper edge 421 of the rear cover sheet 42 (i.e., along an edge of the waist opening 11). The body-fitting elastic members 45 extend almost straight in nearly parallel with the left-right direction and lie between the waist elastic members 44 and the leg elastic members 43.

In the disposable diaper 1, the waist elastic members 44 contract to form waist opening gathers around the waist opening 11, and the leg elastic members 43 contract to form leg opening gathers around respective leg openings 12. In addition, the body-fitting elastic members 45 contract to form body gathers (so-called body fit gathers) on upper parts of the front cover sheet 41 and the rear cover sheet 42.

The disposable diaper 1 further has a front auxiliary elastic member 471 shown in FIG. 1 and a rear auxiliary elastic member 472 shown in FIG. 2. The front auxiliary elastic member 471 and the rear auxiliary elastic member 472 lie between the body-fitting elastic members 45 and the leg elastic members 43 and windingly extend in the left-right direction, and they are bonded on the front cover sheet 41 and the rear cover sheet 42, respectively. The front auxiliary elastic member 471 is located between the two sheets of the front cover sheet 41, and the rear auxiliary elastic member 472 is located between the two sheets of the rear cover sheet 42. Each of them is bonded thereto with hot melt adhesive in a stretched state, in the same way as the above leg elastic members 43 and the like. In the disposable diaper 1, the front auxiliary elastic member 471 and the rear auxiliary elastic member 472 contract to form auxiliary body gathers on lower parts of the front cover sheet 41 and the rear cover sheet 42 (they are also called as body fit gathers.).

Figure 3:
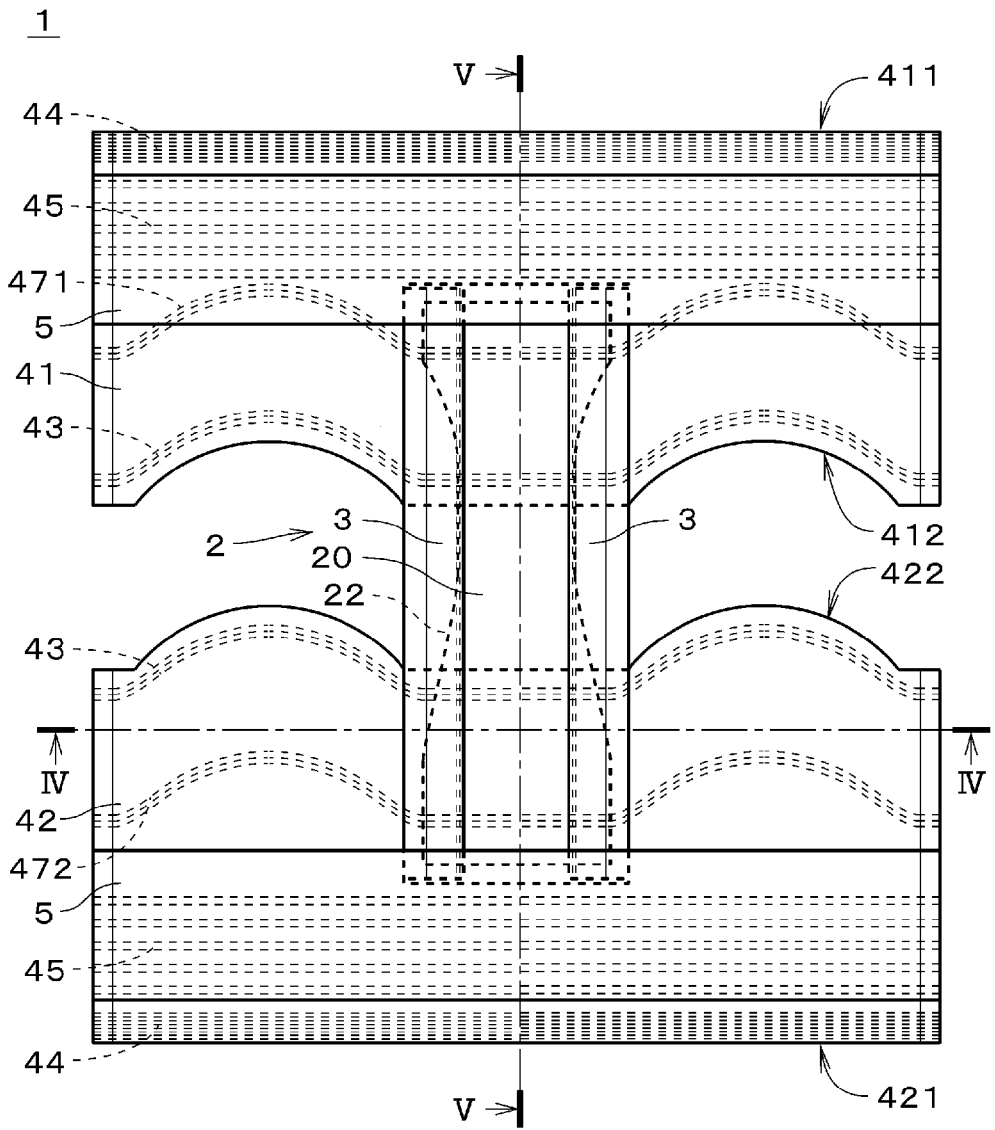
FIG. 3 is a developed view of the disposable diaper.

FIG. 3 is a plan view of the disposable diaper 1, and in FIG. 3, the disposable diaper 1 is viewed from the wearer's side in a developed state where the front cover sheet 41 and the rear cover sheet 42 are separated from each other at both end portions in the left-right direction to be spread (i.e., in a state where the disposable diaper 1 is developed.). The absorbent body 2 is approximately rectangular in a planar view. Both portions of the absorbent body 2 in its longitudinal direction are bonded on surfaces, to face the wearer, of the front cover sheet 41 and the rear cover sheet 42 with hot melt adhesive or the like. Both ends of the absorbent body 2 in the longitudinal direction are covered with two end holding sheets (end sheets) 5, and the two end holding sheets 5 are bonded on the front cover sheet 41 and the rear cover sheet 42, respectively. There may be a case where widths of the end holding sheets 5 in the left-right direction are smaller than those of the front cover sheet 41 and the rear cover sheet 42.

As shown in FIG. 3, in the developed state of the disposable diaper 1, as distance in the left-right direction from the absorbent body 2 increases, the lower edge 412 of the front cover sheet 41 goes (heads) toward the upper edge 411 of the front cover sheet 41 and then goes away from the upper edge 411 (i.e., the lower edge 412 is oriented in a direction toward the upper edge 411 and then oriented in a direction away from the upper edge 411 with increasing distance from the absorbent body 2.). In other words, the lower edge 412 of the front cover sheet 41 is concave so as to be away from the rear cover sheet 42, in each side of the absorbent body 2 in the left-right direction.

As distance in the left-right direction from the absorbent body 2 increases, the lower edge 422 of the rear cover sheet 42 goes away from the upper edge 421 of the rear cover sheet 42 and then goes toward the upper edge 421. In other words, the lower edge 422 of the rear cover sheet 42 is convex toward the front cover sheet 41 in each side of the absorbent body 2 in the left-right direction. The lower edge 412 of the front cover sheet 41 and the lower edge 422 of the rear cover sheet 42 extend almost straight (linearly) in nearly parallel with the left-right direction at areas overlapping with the absorbent body 2.

As described later, the front cover sheet 41 and the rear cover sheet 42 are formed by cutting one sheet member along one cutting line, and edges formed by the cutting process become the lower edge 412 of the front cover sheet 41 and the lower edge 422 of the rear cover sheet 42. Thus, in the developed state of the disposable diaper 1, the lower edge 412 of the front cover sheet 41 has a shape to fit a shape of the lower edge 422 of the rear cover sheet 42 when the front cover sheet 41 and the rear cover sheet 42 are brought close to each other.

As described above, in the front cover sheet 41, since the leg elastic member 43 is located along the lower edge 412 of the front cover sheet 41, the leg elastic member 43 also goes toward the upper edge 411 of the front cover sheet 41 and then goes away from the upper edge 411 with increasing distance from the absorbent body 2 in the left-right direction, in a similar fashion to the lower edge 412 of the front cover sheet 41. In the rear cover sheet 42, since the leg elastic member 43 is located along the lower edge 422 of the rear cover sheet 42, the leg elastic member 43 also goes away from the upper edge 421 of the rear cover sheet 42 and then goes toward the upper edge 421 with increasing distance from the absorbent body 2 in the left-right direction, in a similar fashion to the lower edge 422 of the rear cover sheet 42.

The front auxiliary elastic member 471 has a same shape with the leg elastic member 43 of the front cover sheet 41. Thus, the front auxiliary elastic member 471 goes toward the upper edge 411 of the front cover sheet 41 and then goes away from the upper edge 411 with increasing distance from the absorbent body 2 in the left-right direction. The front auxiliary elastic member 471 is located at a certain distance (almost constant distance) away from the leg elastic member 43 of the front cover sheet 41 toward the upside (i.e., toward the upper edge 411).

The rear auxiliary elastic member 472 has a same shape with the leg elastic member 43 of the rear cover sheet 42. Thus, the rear auxiliary elastic member 472 goes away from the upper edge 421 of the rear cover sheet 42 and then goes toward the upper edge 421 with increasing distance from the absorbent body 2 in the left-right direction. The rear auxiliary elastic member 472 is located at a certain distance (almost constant distance) away from the leg elastic member 43 of the rear cover sheet 42 toward the upside (i.e., toward the upper edge 421). Preferably, the distance, in the up-down direction, between the front auxiliary elastic member 471 and the leg elastic member 43 of the front cover sheet 41, and the distance, in the up-down direction, between the rear auxiliary elastic member 472 and the leg elastic member 43 of the rear cover sheet 42 are equal to or more than 10 millimeters and equal to or less than 100 millimeters.

Figure 4:
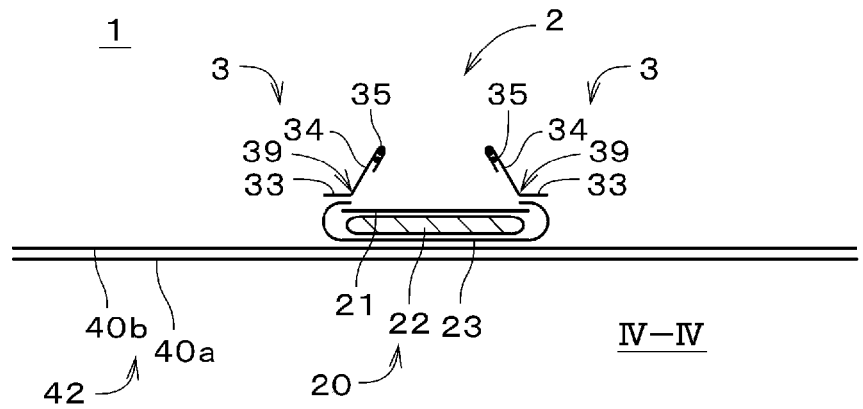
FIG. 4 is a cross-sectional view of the disposable diaper.
Figure 5:
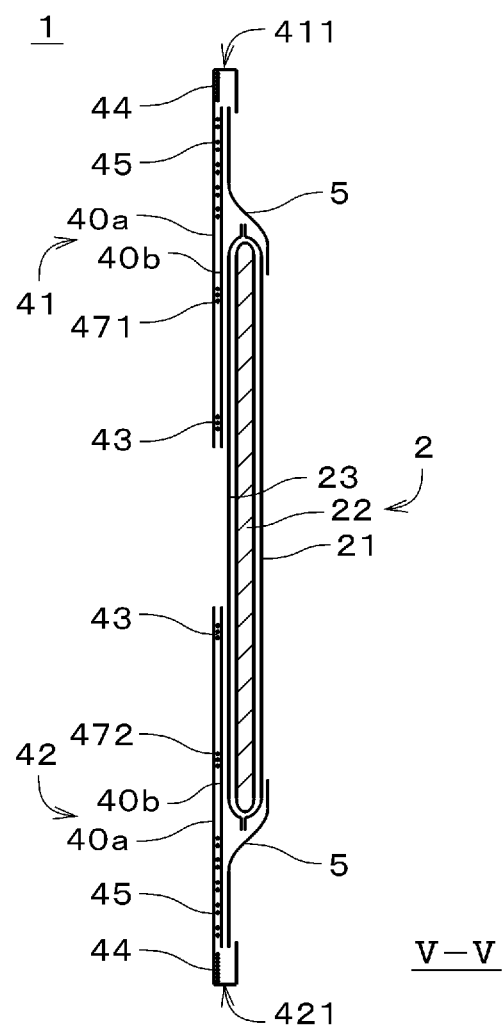
FIG. 5 is a cross-sectional view of the disposable diaper.

FIGS. 4 and 5 are cross-sectional views of the disposable diaper 1 taken along a line IV-IV in FIG. 3 (the line passes through a portion where the absorbent body 2 overlaps with the rear cover sheet 42.) and a line V-V. In FIGS. 4 and 5, respective constituents of the disposable diaper 1 are drawn so as to be slightly apart from one another for the convenience of illustration. As shown in FIGS. 3 and 4, the absorbent body 2 has an approximately sheet-like main body part 20 and a pair of side sheets 3 located on both side portions of the main body part 20, and the pair of side sheets 3 extends across almost the entire length of the main body part 20 in the longitudinal direction. As shown in FIG. 4, the main body part 20 has a top sheet 21, a back sheet 23 and an absorbent core 22 which is located between the top sheet 21 and the back sheet 23. The contour of the absorbent core 22 is drawn by thick broken lines in FIG. 3 for easy understanding of the drawing. As shown in FIG. 3, a width of the absorbent core 22 at each end portion in the longitudinal direction is larger than that at a middle portion of the absorbent core 22 in the longitudinal direction. In other words, the absorbent core 22 is formed in a form of hourglass.

As shown in FIG. 4, each side sheet 3 has a strip-like bonded part 33 and a side wall part 34. The bonded part 33 is one of two portions divided by a folding line 39 extending across almost the entire length thereof in the longitudinal direction and the side wall part 34 is the other of the two portions. The bonded part 33 is located in the vicinity of the side edge of the main body part 20, it lies across almost the entire length thereof in the longitudinal direction, and it is bonded on the wearer's side surface of the main body part 20 with hot melt adhesive. The side wall part 34 is continuous from the bonded part 33 via an inner edge of the bonded part 33 in the left-right direction where the inner edge is the folding line 39. The pair of side wall parts 34 lies on left and right side portions of the main body part 20 and extends across almost the entire length of the main body part 20 in the longitudinal direction.

In both end portions of each side wall part 34 in the longitudinal direction, the side wall part 34 is fixed on the main body part 20 by heat bonding, ultrasonic bonding or bonding with hot melt adhesive. A middle portion of the side wall part 34 in the longitudinal direction is a standing part standing upward from the main body part 20. In the side wall part 34, a standing part elastic member 35 is bonded in a free edge of the standing part, and gathers are formed in the standing part by contraction of the standing part elastic member 35.

As shown in FIGS. 4 and 5, each of the front cover sheet 41 and the rear cover sheet 42 has an outer sheet 40a and an inner sheet 40b, and the inner sheet 40b is laminated on the outer sheet 40a and bonded thereon with hot melt adhesive or the like. As shown in FIG. 5, the leg elastic members 43, the body-fitting elastic members 45, the front auxiliary elastic member 471 and the rear auxiliary elastic member 472 are located between the outer sheets 40a and the inner sheets 40b and bonded to both sheets. In an upper end portion of the front cover sheet 41, the outer sheet 40a is turned toward the inner sheet 40b at a folding line 411 parallel to the left-right direction, and the waist elastic member 44 is located and bonded between the turndown portion of the front cover sheet 41 and a portion facing the turndown portion. Similarly in an upper end portion of the rear cover sheet 42, the outer sheet 40a is turned toward the inner sheet 40b at a folding line 421 parallel to the left-right direction, and the waist elastic member 44 is bonded between two layered portions of the outer sheet 40a. In the disposable diaper 1, the above two folding lines 411, 421 are the upper edge 411 of the front cover sheet 41 and the upper edge 421 of the rear cover sheet 42, respectively. On the inner sheets 40b, the absorbent body 2 having the top sheet 21, the absorbent core 22 and the back sheet 23, and the end holding sheets 5 are bonded with hot melt adhesive or the like.

The top sheet 21 is made of liquid-pervious sheet material, and the top sheet 21 immediately catches moisture of excrement from the wearer and moves the moisture into the absorbent core 22. For example, the top sheet 21 is a liquid-pervious nonwoven fabric made of hydrophobic fibers (polypropylene, polyethylene, polyester, polyamide, nylon or the like) where hydrophilic treatment is performed on its surface with surfactant, and as the nonwoven fabric, for example a point-bond nonwoven fabric, air-through nonwoven fabric or spunbond nonwoven fabric is utilized. A nonwoven fabric (for example, spunlace nonwoven fabric) made of hydrophilic fibers such as cellulose, rayon, cotton may be used as the top sheet 21.

The absorbent core 22 is formed by wrapping a mixture of hydrophilic fibers such as crushed pulp fibers or cellulose fibers and super absorbent material such as granulated super absorbent polymers (e.g., SAP (Super Absorbent Polymer)) or super absorbent fibers, in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap the hydrophilic fibers, is bonded to the hydrophilic fibers and the absorbent material with hot melt adhesive, to prevent deformation of the hydrophilic fibers and falling of the absorbent material (especially, falling after absorption of moisture). In the present embodiment, the absorbent core 22 includes pulp fibers and SAP. A sheet where super absorbent material is bonded between laminated liquid-pervious nonwoven fabrics or the like (so-called polymer sheet) may be used as the absorbent core 22.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers, or a water-repellent or liquid-impervious plastic film. A laminated sheet of the nonwoven fabric and the plastic film may be used. The back sheet 23 prevents moisture of excrement or the like which has come to the back sheet 23, from leaking outside the main body part 20. In a case where a plastic film is used for the back sheet 23, it is preferable that a plastic film with permeability (breathability) is used, from the view point of preventing sweatiness in the disposable diaper 1 and providing comfortable feeling to the wearer.

The side sheet 3 is formed by bonding the standing part elastic member 35 on a side sheet main body made of a nonwoven fabric or a plastic film, with hot melt adhesive or the like. As the side sheet main body, used is for example a water-repellent or liquid-impervious nonwoven fabric (a spunbond nonwoven fabric, meltblown nonwoven fabric, SMS nonwoven fabric or the like) made of hydrophobic fibers. The standing part elastic member 35 has two elastic elements, and for example, a polyurethane yarn, strip-like polyurethane film, yarn-like or strip-like natural rubber, or the like is used as the elastic element. In the present embodiment, polyurethane yarns are used as the elastic elements of the standing part elastic member 35.

A water-repellent or liquid-impervious nonwoven fabric made of hydrophobic fibers, or a water-repellent or liquid-impervious plastic film is used for the outer sheets 40a and the inner sheets 40b of the front cover sheet 41 and the rear cover sheet 42, and the end holding sheets 5, in a similar fashion to the back sheet 23. A laminated sheet of the nonwoven fabric and the plastic film may be used. It is preferable that a film with permeability (breathability) is used as the plastic film. There may be a case where a liquid-pervious nonwoven fabric made of hydrophobic fibers where hydrophilic treatment is performed, or a nonwoven fabric made of hydrophilic fibers is used for the outer sheets 40a and the inner sheets 40b of the front cover sheet 41 and the rear cover sheet 42, and the end holding sheets 5, in a similar fashion to the top sheet 21.

Each of the leg elastic member 43, the front auxiliary elastic member 471 and the rear auxiliary elastic member 472 has three elastic elements, the waist elastic member 44 has eight elastic elements, and the body-fitting elastic member 45 has ten elastic elements. As each elastic element, for example a polyurethane yarn, strip-like polyurethane film, yarn-like or strip-like natural rubber, or the like is used in a similar fashion to the elastic elements of the standing part elastic member 35. In the present embodiment, polyurethane yarns are used as the elastic elements.

Figure 6:
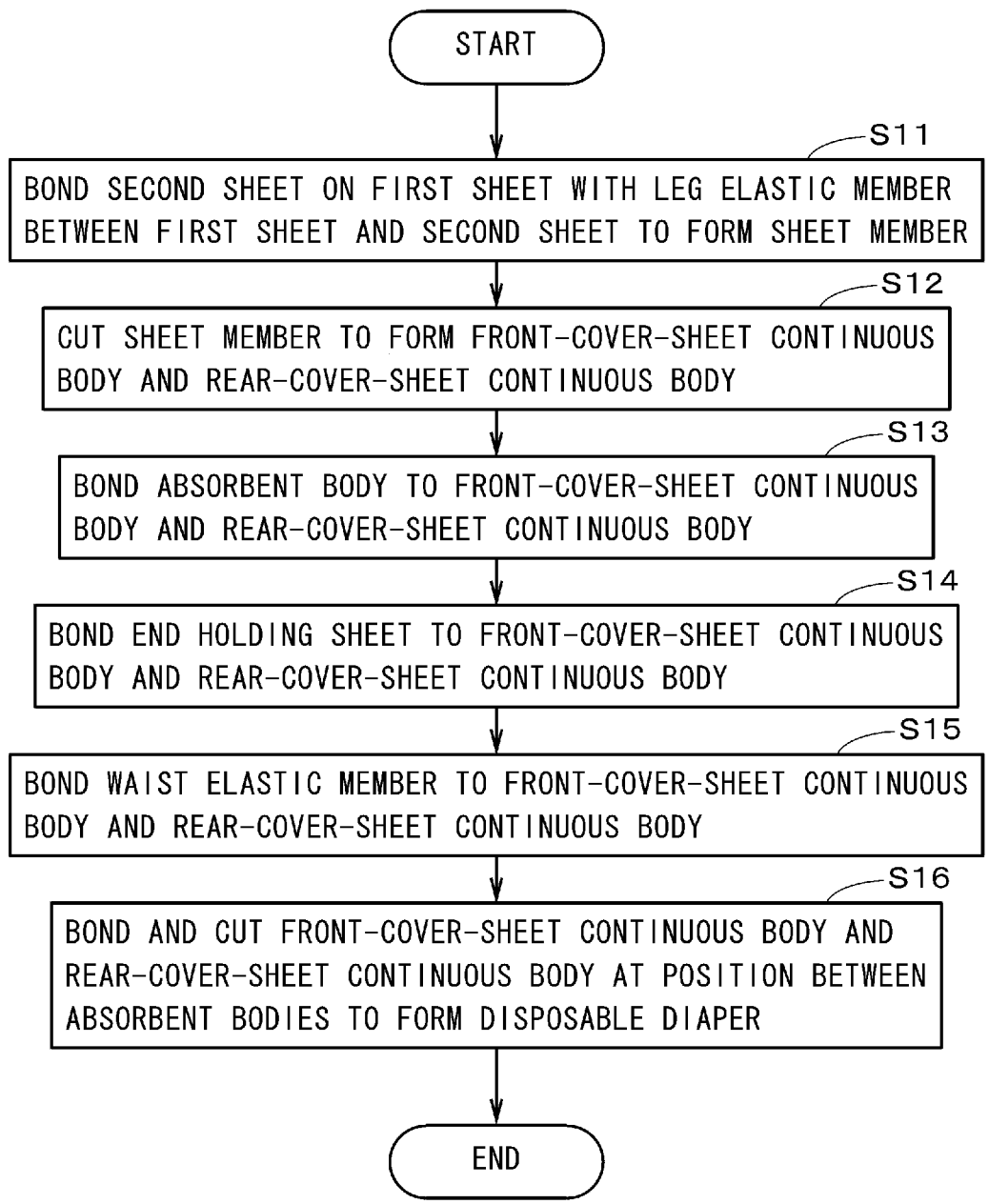
FIG. 6 is a flowchart showing an operation flow for manufacturing a disposable diaper.
Figure 7A:
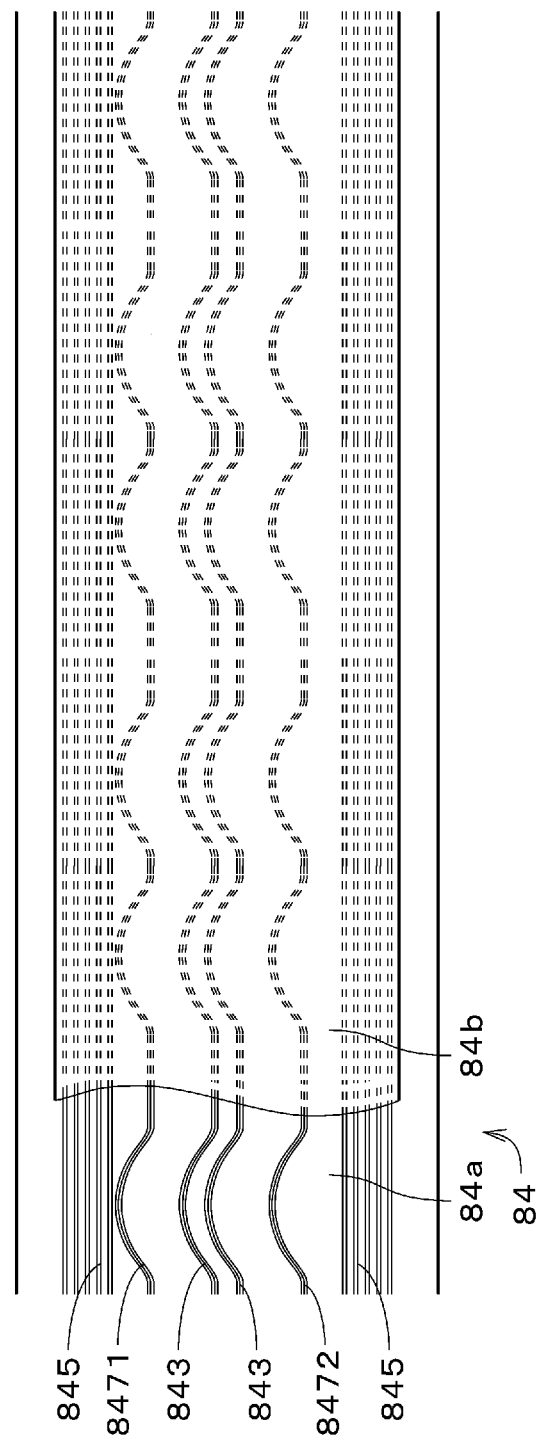
FIG. 7A is a plan view showing the disposable diaper in the course of manufacturing.

Next, discussion will be made on an operation flow for manufacturing the disposable diaper 1 with reference to FIG. 6. FIGS. 7A to 7E are plan views showing the disposable diaper 1 in the course of manufacturing. In manufacture of the disposable diaper 1, conveying a strip-like first sheet 84a from the left side to the right side in FIG. 7A is started. In the following description, a left-right direction in FIG. 7A is referred to as a "conveying direction" and a direction orthogonal to the conveying direction and parallel to the first sheet 84a is referred to as a "width direction" (the same applies to FIGS. 7B to 7E.). The conveying direction is identical to the left-right direction of the disposable diaper 1 shown in FIGS. 1 to 3, and the width direction corresponds to the up-down direction of the disposable diaper 1.

Subsequently, a pair of elastic members 843, a pair of elastic members 845 and elastic members 8471, 8472 are located on the first sheet 84a moving (conveyed) in the conveying direction, and a strip-like second sheet 84b moving in the conveying direction is laid on the first sheet 84a and bonded to the first sheet 84a with these elastic members between the first sheet 84a and the second sheet 84b with hot melt adhesive or the like, to form a strip-like sheet member 84 (step S11). A width of the second sheet 84b in the width direction is smaller than that of the first sheet 84a, and both end portions of the first sheet 84a in the width direction are not covered with the second sheet 84b (i.e., the end portions are exposed.). The elastic members 843, 845, 8471, 8472 are elastic members to become the leg elastic members 43, the body-fitting elastic members 45, the front auxiliary elastic member 471 and the rear auxiliary elastic member 472 of the disposable diaper 1 (see FIG. 3), respectively, and hereinafter they are referred to as the "leg elastic members 843", the "body-fitting elastic members 845", the "front auxiliary elastic member 8471" and the "rear auxiliary elastic member 8472".

The pair of leg elastic members 843 on the first sheet 84a windingly extends along the conveying direction and is located a certain distance away from each other in the width direction. The pair of body-fitting elastic members 845 on the first sheet 84a is located outside the pair of leg elastic members 843 in the width direction and lies in nearly parallel with the conveying direction. The front auxiliary elastic member 8471 and the rear auxiliary elastic member 8472 on the first sheet 84a lie between the pair of body-fitting elastic members 845 and the pair of leg elastic members 843, windingly extend along the conveying direction and are located a certain distance away from each other in the width direction.

Figure 7B:
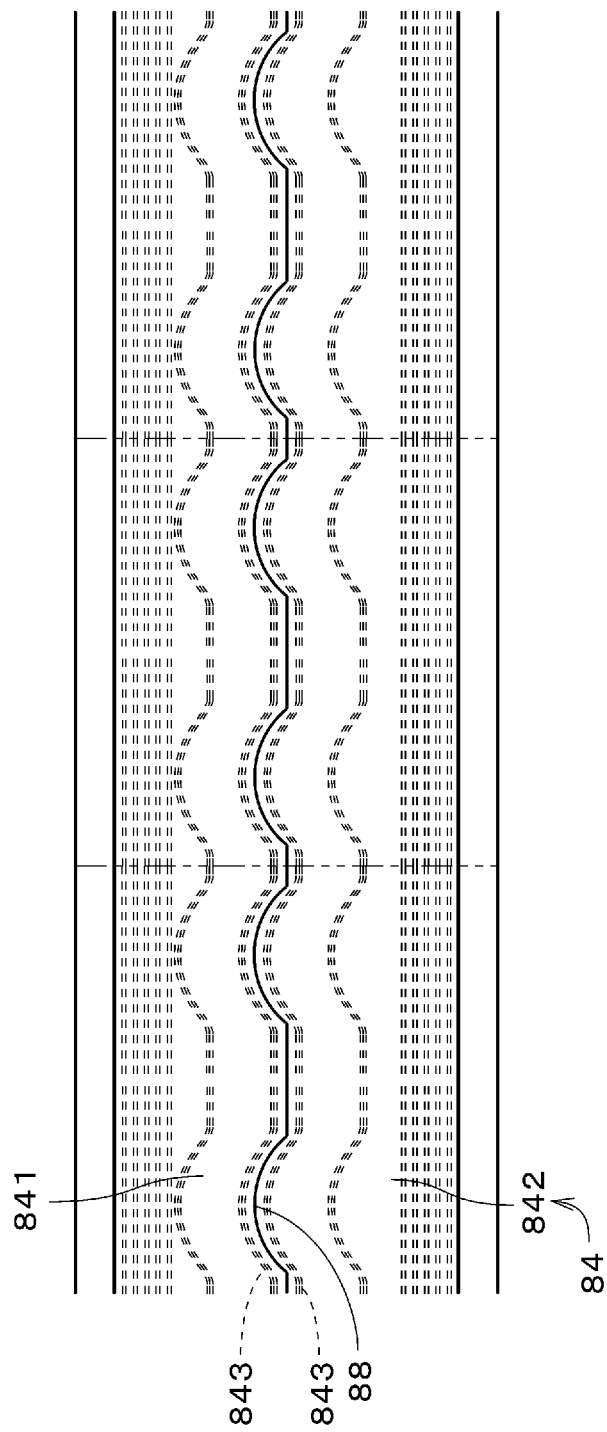
FIG. 7B is a plan view showing the disposable diaper in the course of manufacturing.

Subsequently, as shown in FIG. 7B, the sheet member 84 is cut along a cutting line 88 positioned at almost the center between the pair of leg elastic members 843, to form two sheet members 841, 842 (step S12). In the sheet member 841, a plurality of members each of which is to be the front cover sheet 41 (see FIG. 3) of the disposable diaper 1 are continuous in the conveying direction, and hereinafter the sheet member 841 is referred to as a "front-cover-sheet continuous body 841". In the sheet member 842, a plurality of members each of which is to be the rear cover sheet 42 (see FIG. 3) of the disposable diaper 1 are continuous in the conveying direction, and hereinafter the sheet member 842 is referred to as a "rear-cover-sheet continuous body 842". In other words, the front cover sheet 41 is a part of the front-cover-sheet continuous body 841, and the rear cover sheet 42 is a part of the rear-cover-sheet continuous body 842. In FIG. 7B, boundary positions between the plurality of the front cover sheets 41 (and between the plurality of the rear cover sheets 42) are drawn by chain double-dashed lines for easy understanding of the drawing (the same applies to FIGS. 7C and 7D.).

Figure 7C:
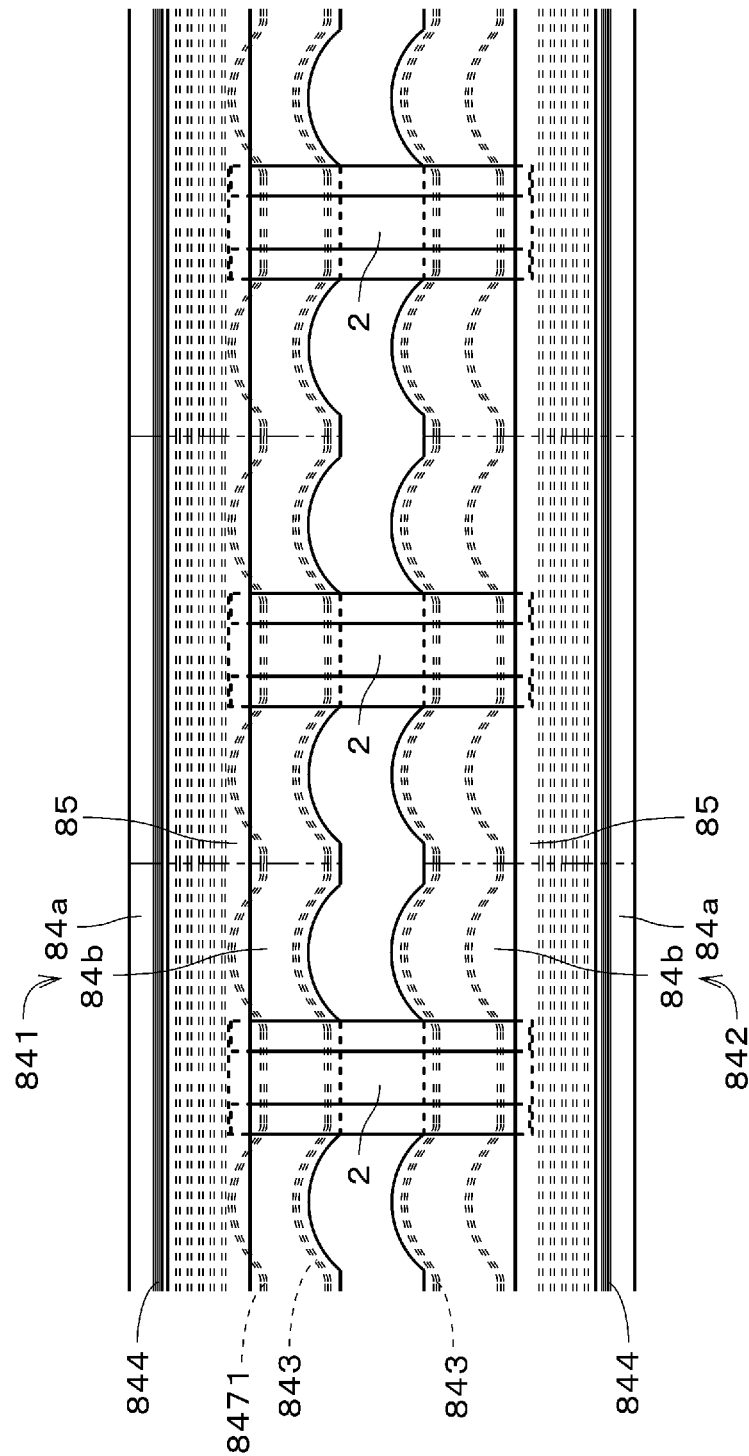
FIG. 7C is a plan view showing the disposable diaper in the course of manufacturing.

Next, as shown in FIG. 7C, the front-cover-sheet continuous body 841 and the rear-cover-sheet continuous body 842 are brought away from each other in the width direction, and a plurality of absorbent bodies 2 are sequentially located between the front-cover-sheet continuous body 841 and the rear-cover-sheet continuous body 842, to bond the plurality of absorbent bodies 2 to the front-cover-sheet continuous body 841 and the rear-cover-sheet continuous body 842 (step S13). And two strip-like sheet members 85 extending in the conveying direction are bonded on the second sheets (separated second sheets) 84b of the front-cover-sheet continuous body 841 and the rear-cover-sheet continuous body 842 with both ends of the plurality of absorbent bodies 2 between the sheet members 85 and the second sheets 84b (step S 14). The sheet members 85 are members to be the end holding sheets 5 of the disposable diapers 1 and hereinafter referred to as "end holding sheets 85". In the front-cover-sheet continuous body 841 and the rear-cover-sheet continuous body 842, before each absorbent body 2 is bonded, portions of the leg elastic members 843, the front auxiliary elastic member 8471 and the rear auxiliary elastic member 8472 which overlap with the absorbent body 2, are cut at a plurality of positions (so-called "dot cutting" are performed) as appropriate, so that forces of contraction in the portions are lost.

After bonding the absorbent bodies 2 and the end holding sheets 85, a pair of elastic members 844 in nearly parallel with the conveying direction is located on portions of the first sheets (separated first sheets) 84a which are not covered with the second sheets 84b and which are included in outer portions (i.e., portions lying outermost in the width direction) of the front-cover-sheet continuous body 841 and the rear-cover-sheet continuous body 842. The elastic members 844 are elastic members to be waist elastic members 44 of the disposable diaper 1 and hereinafter they are referred to as "waist elastic members 844".

Figure 7D:
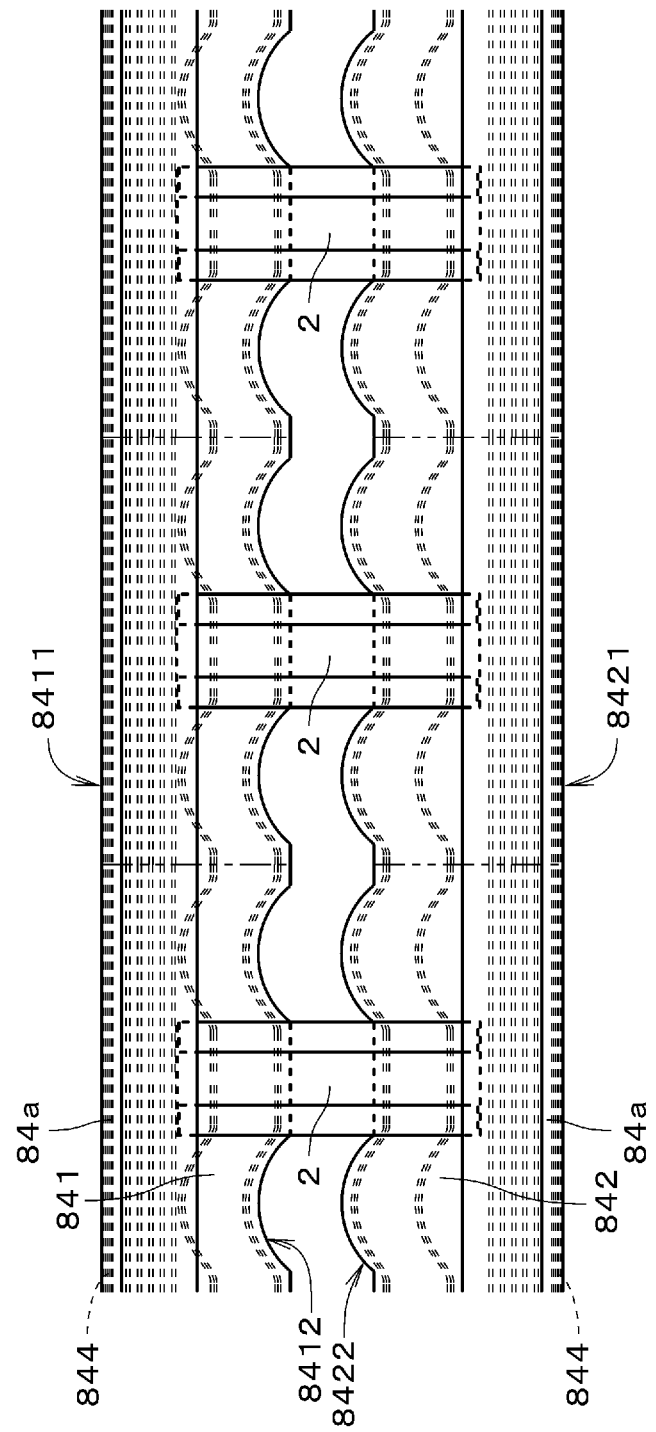
FIG. 7D is a plan view showing the disposable diaper in the course of manufacturing.

As shown in FIG. 7D, the outer portions of the first sheets 84a in the front-cover-sheet continuous body 841 and the rear-cover-sheet continuous body 842 are turned (folded back) inward in the width direction along folding lines 8411, 8421 lying outside respective waist elastic members 844 and being in nearly parallel with the conveying direction, so that the waist elastic members 844 are located therebetween. The waist elastic members 844 are bonded in the double-layered portions of the first sheets 84a (step S 15). The folding lines 8411, 8421 which are edges lying outermost in the width direction are hereinafter referred to as "outer edges 8411, 8421". The pair of waist elastic members 844 is located along the outer edges 8411, 8421.

In the front-cover-sheet continuous body 841, a cut edge 8412 which is formed by cutting in the above step S12 is a continuous line of the lower edges 412 (see FIG. 3) of the front cover sheets 41. When in the front-cover-sheet continuous body 841, only a portion which is to be one front cover sheet 41 is noted, as distance on each side of the conveying direction from the absorbent body 2 increases, the cut edge 8412 goes toward the outer edge 8411 (i.e., the upper edge 411 of the front cover sheet 41) of the front-cover-sheet continuous body 841 and then goes away from the outer edge 8411. The cut edge 8412 extends almost straight in nearly parallel with the conveying direction at an area overlapping with the absorbent body 2.

In the rear-cover-sheet continuous body 842, a cut edge 8422 which is formed by cutting in the above step S12 is a continuous line of the lower edges 422 (see FIG. 3) of the rear cover sheets 42. When in the rear-cover-sheet continuous body 842, only a portion which is to be one rear cover sheet 42 is noted, as distance on each side of the conveying direction from the absorbent body 2 increases, the cut edge 8422 goes away from the outer edge 8421 (i.e., the upper edge 421 of the rear cover sheet 42) of the rear-cover-sheet continuous body 842 and then goes toward the outer edge 8421. The cut edge 8422 extends almost straight in nearly parallel with the conveying direction at an area overlapping with the absorbent body 2.

Figure 7E:
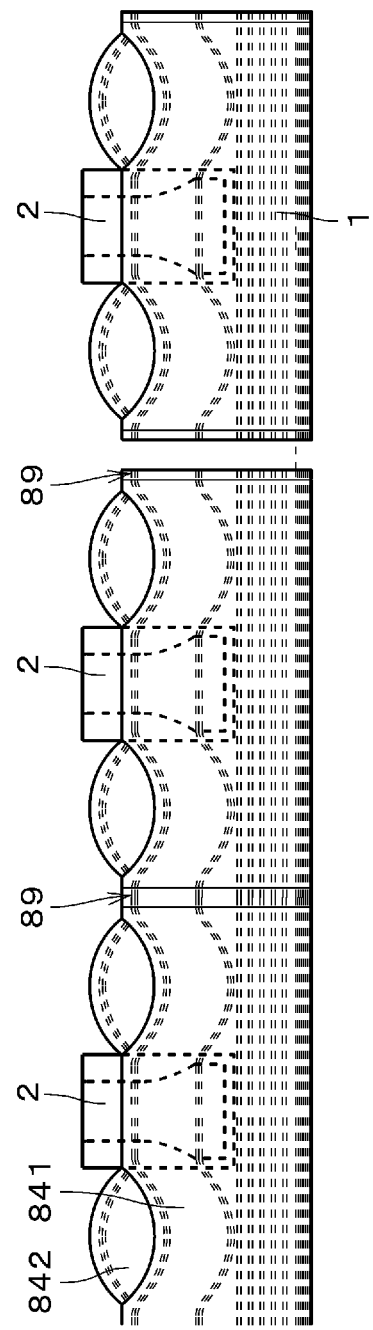
FIG. 7E is a plan view showing the disposable diaper in the course of manufacturing.

After bonding the waist elastic members 844, as shown in FIG. 7E, the plurality of absorbent bodies 2 are sequentially folded to lay (overlap) the front-cover-sheet continuous body 841 on the rear-cover-sheet continuous body 842. Then, the front-cover-sheet continuous body 841 and the rear-cover-sheet continuous body 842 are bonded to each other by heat bonding, ultrasonic bonding or the like at narrow strip-like bonding areas 89 extending in the width direction and lying between the plurality of absorbent bodies 2. After that, the front-cover-sheet continuous body 841 and the rear-cover-sheet continuous body 842 are cut at the plurality of bonding areas 89 (i.e., bonding positions), to sequentially form a plurality of disposable diapers 1 (step S16). Actually, in portions corresponding to the upper portions of the cover sheets 4, the front-cover-sheet continuous body 841 and the rear-cover-sheet continuous body 842 are indirectly bonded to each other through the end holding sheets 85.

As described above, in the state of the disposable diaper 1 where the front cover sheet 41 and the rear cover sheet 42 are separated from each other to be developed (i.e., the developed state of the disposable diaper 1), as distance in the left-right direction from the absorbent body 2 increases, the lower edge 422 of the rear cover sheet 42 goes away from the upper edge 421 of the rear cover sheet 42 and then goes toward the upper edge 421. And in left and right of the absorbent body 2, the leg elastic member 43 is bonded on the rear cover sheet 42 so as to lie along the lower edge 422 of the rear cover sheet 42. As above, in the disposable diaper 1, the lower end portion of the rear cover sheet 42 has a downwardly convex shape in each of left and right of the absorbent body 2, and the lower portions of hips of the wearer (they may include the neighborhoods of the borders between the hips and thighs.) are fully wrapped with the lower end portion. It is therefore possible to suppress leakage of excrement from the lower portions of hips of the wearer (i.e., leakage of excrement from the rear-lower portion of the disposable diaper 1).

In the developed state of the disposable diaper 1, as distance in the left-right direction from the absorbent body 2 increases, the lower edge 412 of the front cover sheet 41 goes toward the upper edge 411 of the front cover sheet 41 and then goes away from the upper edge 411. As above, in the front side of the disposable diaper 1, each leg opening 12 has an upwardly arched shape at its middle portion in the left-right direction (i.e., an edge of portion surrounding leg is formed in concave.). It is therefore possible to prevent the lower end portion of the front cover sheet 41 from interfering with leg movement of the wearer.

As above, in the developed state of the disposable diaper 1, the lower edge 412 of the front cover sheet 41 has a same shape as the lower edge 422 of the rear cover sheet 42. Thus, as the above embodiment, by cutting one sheet member 84 along one cutting line 88, the front cover sheet 41 and the rear cover sheet 42 can be formed at the same time and manufacture of the disposable diaper 1 can be simplified. Furthermore, in formation of the front cover sheet 41 and the rear cover sheet 42, since any portion of the sheet member 84 is not cut away to be discarded, manufacturing cost of the disposable diaper 1 can be reduced.

In the disposable diaper 1, the lower edge 412 of the front cover sheet 41 and the lower edge 422 of the rear cover sheet 42 extend almost straight in nearly parallel with the left-right direction at the areas overlapping with the absorbent body 2. As above, the lower edges 412, 422 of the front cover sheet 41 and the rear cover sheet 42 have almost straight shapes at areas which do not affect functions of the disposable diaper 1 such as increase in freedom of leg movement and prevention of leakage, and therefore shapes of the front cover sheet 41 and the rear cover sheet 42 can be simplified. In addition to that, since the cutting line 88 in cutting the sheet member 84 is shortened, manufacture of the disposable diaper 1 can be made easy.

As above, the leg elastic members 43 are located along the lower edges 412, 422 of the front cover sheet 41 and the rear cover sheet 42, the front auxiliary elastic member 471 and the rear auxiliary elastic member 472 have same shapes as the leg elastic members 43, and the leg elastic members 43, the front auxiliary elastic member 471 and the rear auxiliary elastic member 472 extend almost straight in nearly parallel with the left-right direction at the areas overlapping with the absorbent body 2. Thus, since the entire lengths of the leg elastic members 43, the front auxiliary elastic member 471 and the rear auxiliary elastic member 472 are shortened, manufacturing cost of the disposable diaper 1 can be reduced. In addition, at the areas overlapping with the absorbent body 2, the dot cutting for the leg elastic members 43, the front auxiliary elastic member 471 and the rear auxiliary elastic member 472 can be performed easily and surely.

In the disposable diaper 1, since the front auxiliary elastic member 471 is provided between the leg elastic member 43 and the body-fitting elastic member 45 in the front cover sheet 41, the lower portion of the front cover sheet 41 can be brought into close contact with the wearer. Since the rear auxiliary elastic member 472 is provided between the leg elastic member 43 and the body-fitting elastic member 45 in the rear cover sheet 42, the lower portion of the rear cover sheet 42 can be brought into close contact with the wearer. The front auxiliary elastic member 471 and the rear auxiliary elastic member 472 curvedly extend, and therefore portions, in wide ranges of the up-down direction, of the front cover sheet 41 and the rear cover sheet 42 can be brought into close contact with the wearer.

As above, in the disposable diaper 1, it is possible to suppress leakage of excrement from a lower portion of the back side of the wearer. Thus, structure of the disposable diaper 1 is especially suitable for a pants-type disposable diaper which is often used by an ambulatory wearer who takes various body positions. In the disposable diaper 1, the lower end portion of the front cover sheet 41 can be prevented from interfering with leg movement of the wearer. Also from this viewpoint, it is considered that structure of the disposable diaper 1 is especially suitable for a pants-type disposable diaper.

Though the preferred embodiments of the present invention have been discussed above, the present invention is not limited to the above-discussed preferred embodiments, but allows various variations.

For example, the lower edges 412, 422 of the front cover sheet 41 and the rear cover sheet 42 do not necessarily lie across the entire lengths of the areas overlapping with the absorbent body 2, in a linear fashion parallel with the left-right direction. In the case where the width of the absorbent body 2 in the left-right direction is larger than that shown in FIG. 3 or the like, a side portion of the absorbent body 2 may overlap with curving portions of the lower edges 412, 422. The lower edges 412, 422 may be made non-straight across the entire lengths, in the left-right direction, of the areas overlapping with the absorbent body 2 as appropriate.

The front auxiliary elastic member 471 is not necessarily brought away in the up-down direction from the body-fitting elastic member 45, and for example a portion, which is close to the upper edge 411, of the front auxiliary elastic member 471 may be overlapped with the body-fitting elastic member 45. In the disposable diaper 1, either or both the front auxiliary elastic member 471 and the rear auxiliary elastic member 472 may be omitted, if the lower portion(s) of the cover sheet 4 can be sufficiently brought into close contact with the wearer.

Figure 8:
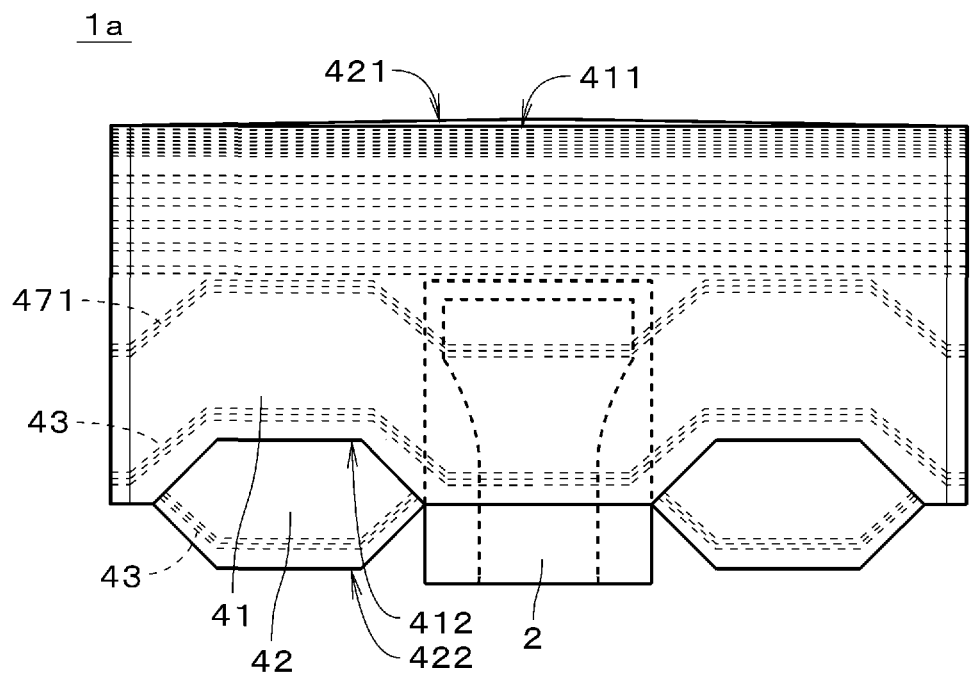
FIG. 8 is a front view of another disposable diaper.

In the above disposable diaper 1, the leg elastic members 43, the front auxiliary elastic member 471 and the rear auxiliary elastic member 472, and the lower edge 412 of the front cover sheet 41 and the lower edge 422 of the rear cover sheet 42 are almost arc-like on each side of the absorbent body 2 in the left-right direction, however they may be other various shapes. For example, in a developed state of a disposable diaper 1a shown in FIG. 8, with increasing distance from the absorbent body 2 in the left-right direction, the lower edge 412 of the front cover sheet 41, the leg elastic member 43 and the front auxiliary elastic member 471 go in a direction toward the upper edge 411 of the front cover sheet 41 in a linear fashion, subsequently go in a direction in nearly parallel with the left-right direction in a linear fashion, and then go in a direction away from the upper edge 411 of the front cover sheet 41 in a linear fashion. The lower edge 422 of the rear cover sheet 42, the leg elastic member 43 and the rear auxiliary elastic member (not shown) go in a direction away from the upper edge 421 of the rear cover sheet 42 in a linear fashion, subsequently go in a direction in nearly parallel with the left-right direction in a linear fashion, and then go in a direction toward the upper edge 421 of the rear cover sheet 42 in a linear fashion, with increasing distance from the absorbent body 2 in the left-right direction.

In manufacture of the disposable diaper 1, there may be a case where widths of the first sheet 84a and the second sheet 84b in the width direction are equal to each other and the waist elastic members 844 are bonded between the first sheet 84a and the second sheet 84b in step S11 in the same way as the leg elastic members 843 and the like. The body-fitting elastic members 845 may be located and bonded not between the first sheet 84a and the second sheet 84b but between the second sheet 84b and the end holding sheets 85.

In the disposable diaper 1, the lower edge 412 of the front cover sheet 41 does not necessarily have a same shape as the lower edge 422 of the rear cover sheet 42. For example, if it is preferred that a portion, covering the vicinity of the groin (the base of the legs) on the front side, of the front cover sheet 41 is made larger, on both left and right sides of the absorbent body 2, the lower edge 412 of the front cover sheet 41 may be made straight in nearly parallel with the left-right direction without change of shape of the lower edge 422 in the rear cover sheet 42. In this case, the front cover sheet 41 and the rear cover sheet 42 can be formed not only by cutting one sheet member into two at one cutting line, but also by removing an unnecessary portion from the one sheet or the like.

In the disposable diaper 1, both side portions (i.e., both end portions in the left-right direction) of the front cover sheet 41 are not necessarily bonded to both side portions of the rear cover sheet 42. For example, there may be a case where fastening tapes are provided on the both side portions of the rear cover sheet 42, the fastening tapes are fastened on an attachment part provided on the outer surface of the front cover sheet 41 and therefore the both side portions of the front cover sheet 41 are connected to the both side portions of the rear cover sheet 42. In other words, the disposable diaper 1 may be an open-type (tape-type) disposable diaper where the both side portions of the front cover sheet 41 are connectable to the both side portions of the rear cover sheet 42.

In the pants-type disposable diaper 1, there may be a case where an attachment part is provided on the outer surface of the front cover sheet 41, weakening lines such as perforations each extending in the up-down direction are formed in left and right of the attachment part on the front cover sheet and the fastening parts are provided on portions lying outside respective weakening lines in the left-right direction. In beginning of use, the disposable diaper having such structure is worn as pants-type. When a caregiver or the like confirms a state of the inside, the front cover sheet 41 is cut at the weakening lines and the state of the inside is confirmed. At this time, if excretion has not been performed and the disposable diaper can be used continuously, the fastening parts lying outside the weakening lines are fastened on the attachment part to continue using the disposable diaper. In addition, structure of the disposable diaper 1 can be adapted to various absorbent products such as a disposable sanitary diaper.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST 1, 1a disposable diaper
2 absorbent body
41 front cover sheet
42 rear cover sheet
43 leg elastic member
44 waist elastic member
45 body-fitting elastic member
84 sheet member
411, 421 upper edge
412, 422 lower edge
471 front auxiliary elastic member
472 rear auxiliary elastic member
841 front-cover-sheet continuous body
842 rear-cover-sheet continuous body
843 leg elastic member
844 waist elastic member
8411, 8421 outer edge
8412, 8422 cut edge
S11 to S16 step

The invention claimed is:
1. An absorbent product, comprising:
a rear cover sheet;
a front cover sheet whose both side portions in a left-right direction are bonded or connectable to both side portions of said rear cover sheet in said left-right direction;
an absorbent body which extends from a front middle portion of said front cover sheet to a rear middle portion of said rear cover sheet via a crotch portion of a wearer when worn, said front middle portion being a middle portion in said left-right direction, said rear middle portion being a middle portion in said left-right direction;
waist elastic members which are bonded on said front cover sheet and said rear cover sheet along an upper edge of said front cover sheet and an upper edge of said rear cover sheet, said waist elastic members forming waist opening gathers around a waist opening;
leg elastic members which are bonded on said front cover sheet and said rear cover sheet in left and right of said absorbent body, said leg elastic members lying along a lower edge of said front cover sheet and a lower edge of said rear cover sheet, said leg elastic members forming by contraction leg opening gathers around respective leg openings, each of said leg elastic members including elastic elements adjacent to each other;
body-fitting elastic members extending in said left-right direction, lying between said waist elastic members and said leg elastic members and being bonded on said front cover sheet and said rear cover sheet, said body-fitting elastic members forming by contraction body gathers on said front cover sheet and said rear cover sheet; and
a rear auxiliary elastic member lying between a body-fitting elastic member and a leg elastic member being bonded on said rear cover sheet at a distance away from said leg elastic member, said distance being larger than a distance between adjacent elastic elements of said leg elastic member, said rear auxiliary elastic member forming by contraction auxiliary body gathers on said rear cover sheet; wherein
in a developed state where said front cover sheet and said rear cover sheet are separated from each other to be developed, as distance in said left-right direction from said absorbent body increases, said lower edge of said rear cover sheet goes away from said upper edge of said rear cover sheet and then goes toward said upper edge and said rear auxiliary elastic member goes away from said upper edge and then goes toward said upper edge.

2. The absorbent product according to claim 1, wherein in a developed state where said front cover sheet and said rear cover sheet are separated from each other to be developed, as distance in said left-right direction from said absorbent body increases, said lower edge of said front cover sheet goes toward said upper edge of said front cover sheet and then goes away from said upper edge.

3. The absorbent product according to claim 2, further comprising:
a front auxiliary elastic member having a same shape with a leg elastic member bonded on said front cover sheet, lying between a body-fitting elastic member and said leg elastic member and being bonded on said front cover sheet at a certain distance away from said leg elastic member.

4. The absorbent product according to claim 2, wherein in a developed state where said front cover sheet and said rear cover sheet are separated from each other to be developed, said lower edge of said front cover sheet has a shape to fit a shape of said lower edge of said rear cover sheet when said front cover sheet and said rear cover sheet are brought close to each other.

5. The absorbent product according to claim 4, further comprising:
a front auxiliary elastic member having a same shape with a leg elastic member bonded on said front cover sheet, lying between a body-fitting elastic member and said leg elastic member and being bonded on said front cover sheet at a certain distance away from said leg elastic member.

6. The absorbent product according to claim 2, wherein said lower edge of said front cover sheet and said lower edge of said rear cover sheet extend straight in parallel with said left-right direction at areas overlapping with said absorbent body.

7. The absorbent product according to claim 6, further comprising:
a front auxiliary elastic member having a same shape with a leg elastic member bonded on said front cover sheet, lying between a body-fitting elastic member and said leg elastic member and being bonded on said front cover sheet at a certain distance away from said leg elastic member.

8. The absorbent product according to claim 1, further comprising:
a front auxiliary elastic member having a same shape with a leg elastic member bonded on said front cover sheet, lying between a body-fitting elastic member and said leg elastic member and being bonded on said front cover sheet at a certain distance away from said leg elastic member.

9. The absorbent product according to claim 1, wherein both side portions of said front cover sheet in said left-right direction are bonded to both side portions of said rear cover sheet in said left-right direction.

10. The absorbent product according to claim 9, further comprising:
a front auxiliary elastic member having a same shape with a leg elastic member bonded on said front cover sheet, lying between a body-fitting elastic member and said leg elastic member and being bonded on said front cover sheet at a certain distance away from said leg elastic member.

11. A method of manufacturing an absorbent product, comprising the steps of:
a) forming a sheet member by locating a pair of leg elastic members, a pair of body-fitting elastic members and a rear auxiliary elastic member on a strip-like first sheet and bonding a strip-like second sheet on said first sheet with said pair of leg elastic members, said pair of body-fitting elastic members and said rear auxiliary elastic member between said first sheet and said second sheet while conveying said first sheet in a predetermined conveying direction, said pair of leg elastic members windingly extending along said conveying direction and being located a certain distance away from each other in a width direction orthogonal to said conveying direction, said pair of body-fitting elastic members being located outside said pair of leg elastic members in said width direction and lying in nearly parallel with said conveying direction, said rear auxiliary elastic member lying, between a body-fitting elastic member and a leg elastic member, at a distance away from said leg elastic member, said leg elastic member including elastic elements adjacent to each other, said distance being larger than a distance between adjacent elastic elements of said leg elastic member;
b) forming a front-cover-sheet continuous body and a rear-cover-sheet continuous body by cutting said sheet member between said pair of leg elastic members;
c) bringing said front-cover-sheet continuous body and said rear-cover-sheet continuous body away from each other in said width direction and sequentially locating a plurality of absorbent bodies between said front-cover-sheet continuous body and said rear-cover-sheet continuous body, to bond said plurality of absorbent bodies to said front-cover-sheet continuous body and said rear-cover-sheet continuous body; and
d) sequentially forming absorbent products by sequentially folding said plurality of absorbent bodies to lay said front-cover-sheet continuous body on said rear-cover-sheet continuous body, bonding said front-cover-sheet continuous body and said rear-cover-sheet continuous body to each other at bonding positions between said plurality of absorbent bodies, and cutting said front-cover-sheet continuous body and said rear-cover-sheet continuous body at said bonding positions; wherein
in a rear cover sheet, which is a portion of said rear-cover-sheet continuous body, of each absorbent product, as distance on each side of said conveying direction from an absorbent body increases, a cut edge formed by cutting in said step b) goes away from an outer edge of said rear-cover-sheet continuous body in said width direction and then goes toward said outer edge and said rear auxiliary elastic member goes away from said outer edge and then goes toward said outer edge,
in a front cover sheet, which is a portion of said front-cover-sheet continuous body, of said each absorbent product, as distance on each side of said conveying direction from said absorbent body increases, a cut edge formed by cutting in said step b) goes toward an outer edge of said front-cover-sheet continuous body in said width direction and then goes away from said outer edge, and
in said each absorbent product, leg elastic members form by contraction leg opening gathers around respective leg openings, body-fitting elastic members form by contraction body gathers on said front cover sheet and said rear cover sheet, and said rear auxiliary elastic member forms by contraction auxiliary body gathers on said rear cover sheet.

12. The method of manufacturing an absorbent product according to claim 11, wherein said cut edge of said front cover sheet and said cut edge of said rear cover sheet extend straight in parallel with said conveying direction at areas overlapping with said absorbent body.

\* \* \* \* \*